United States Patent [19]

Wan et al.

[11] Patent Number: 5,215,634
[45] Date of Patent: Jun. 1, 1993

[54] MICROWAVE INDUCED CATALYTIC CONVERSION OF METHANE AND A HYDRATING AGENT TO $C_3$ OXYGENATES

[75] Inventors: Jeffrey K. S. Wan; Man Y. Ise; Mary C. Depew, all of Kingston, Canada

[73] Assignee: Alberta Oil Sands Technology and Research Authority, Edmonton, Canada

[21] Appl. No.: 625,032

[22] Filed: Dec. 10, 1990

[51] Int. Cl.$^5$ .................. C07C 29/00; C07C 37/00
[52] U.S. Cl. ........................ 204/157.9; 204/157.93
[58] Field of Search ................... 204/157.9, 157.93; 567/403, 383, 910.5, 910

[56] References Cited

U.S. PATENT DOCUMENTS

| | | | |
|---|---|---|---|
| 4,279,722 | 7/1981 | Kirkbride | 204/157.15 |
| 4,574,038 | 3/1986 | Wan | 585/500 |
| 4,618,732 | 10/1986 | Gesser et al. | 568/910.5 |
| 4,975,164 | 12/1990 | Ravella et al. | 204/157.43 |

Primary Examiner—W. Gary Jones
Assistant Examiner—Dean Nguyen
Attorney, Agent, or Firm—Dressler, Goldsmith, Shore, Sutker & Milnamow, Ltd.

[57] ABSTRACT

A process is provided for selectively converting methane and a hydrating agent to $C_3$ to oxygenates. More particularly, methane is reacted with water in the presence of a nickel metal powder catalyst using microwave irradiation to produce acetone and propanol.

7 Claims, No Drawings

MICROWAVE INDUCED CATALYTIC CONVERSION OF METHANE AND A HYDRATING AGENT TO $C_3$ OXYGENATES

FIELD OF THE INVENTION

The present invention relates to a process for selectively converting methane in the presence of a hydrating agent to $C_3$ oxygenates using microwave irradiation.

BACKGROUND OF THE INVENTION

Alcohols are important starting materials in aliphatic chemistry because of the versatility of their reactions. The two principal sources of obtaining simple alcohols are the hydration of alkenes obtained from the cracking of petroleum and the fermentation of carbohydrates.

Acetone, an important solvent is generally prepared by the dehydrogenation of the corresponding alcohol, although other synthetic methods may sometimes be utilized.

The petrochemical industry, in certain areas of the world, exemplary of which is Alberta, Canada, relies on the occurrence of ethane in natural gas as its main source of ethylene. Typically, natural gas would have a two to four percent ethane content. During recent years, it has been observed that the ethane content of produced natural gas has been less.

However, methane, thermodynamically the most stable hydrocarbon, occurs in abundance in natural gas. It would be most desirable to effect conversion of methane to the $C_3$ oxygenates described supra directly using a simple inexpensive method with high conversion rates.

Such a conversion is highly endothermic, requiring high reaction temperatures to convert or react the methane with a hydrating agent such as water. Additionally, at these high temperatures the water would be in the gaseous form and the HOH bond would be difficult to break. Additionally, oxygen would be required and it is deleteriously corrosive or explosive or the like.

During earlier work described in my U.S. Pat. No. 4,574,038, the disclosures of which are herein incorporated by reference, it was discovered that methane could be selectively converted to ethylene and hydrogen using a microwave-induced catalytic hydrocracking process. The process relied on the use of a catalyst adapted both to provide catalytic sites for the hydrocracking reaction and to absorb microwave radiation. The favoured catalyst comprised a 1 micron particle sized mixture of 15% Fe and 85% Ni. Energy in the form of pulsed microwave radiation was supplied to the reaction zone. The duration of the application of energy was controlled to attain selectivity of the conversion.

SUMMARY OF THE INVENTION

In accordance with the present invention there is provided a microwave-induced catalytic process for selectively converting methane and a hydrating agent, typically water, to $C_3$ oxygenates. More specifically the $C_3$ oxygenates yielded comprised acetone, propanol and other liquid products. This process preferably involves the use of a substantially pure nickel powder catalyst to both provide catalytic sites and absorb the microwave radiation. In a more preferred embodiment, there is provided beneath the nickel catalyst a supporting sub-layer of a hydrated salt. Without being bound by same, it appears that such hydrated salt is functional to act as a 'coolant', preventing the converted products from reacting further. The most preferred hydrated salt for use in the sub-layer has been found to be $CaSO_4.2H_2O$. In using this sub-layer beneath the nickel powder catalyst, a higher conversion rate than when nickel alone is used, is obtained.

During the reaction, the microwave radiation is supplied in a pulse train, for a duration and under reaction conditions selected to yield the desired products.

As a result of practicing this process it has been found that one can selectively obtain the $C_3$ oxygenates, substantially without producing any $C_2$ oxygenates or other hydrocarbons.

In a broad aspect, the invention relates to a process for selectively converting methane to $C_3$ oxygenates comprising: providing methane in a reaction zone containing a catalyst functional to absorb microwave radiation; providing a hydrating agent within said reaction zone; irradiating the methane and hydrating agent reactants in the presence of said catalyst with a pulsed microwave irradiation for a sufficient period of time to thereby selectively convert said reactants to $C_3$ oxygenates; and recovering said reaction products.

DESCRIPTION OF THE PREFERRED EMBODIMENT

In accordance with the laboratory procedure, pure, dried methane gas was introduced into the reaction zone at a pressure of between 0.3 to 0.5 atmospheres.

A fixed catalytic bed system was used. More specifically, the catalyst bed contained 100% nickel powder of between 1 to 2000 micron particle size. Alternatively, one could select catalyst from the following either singly or in admixture: Fe, Co, Cu, CuO, $V_2O_5$ powders.

The water was introduced into the reactor by aspirating it as fine droplets onto the surface of the catalyst bed before and during the microwave pulse train application.

A sub-layer comprising a hydrated salt was optionally positioned beneath the metal powder catalyst. Selection of a suitable hydrated salt would be within the skill of the art but $CaSO_4.2H_2O$ was found to be $C_3$ oxygenate selective with high methane conversion rates.

The microwave source used provided 1.5–3.0 GHz with an 80–100 watt incident power level. The total irradiation time used was 25 seconds, with 2.5 second on-time pulses and off-time periods of 25 to 35 seconds.

EXAMPLE

A fixed bed of catalyst, comprising 0.1 g of nickel powder, was provided. A sub-layer comprising 0.3 g water saturated calcium sulphate was placed beneath the catalyst in the reactor. The reactor was positioned in a microwave oven. 0.2 atmospheres of methane was introduced into the reactor. The total irradiation time was 25 seconds. The products from the reaction, which comprised 70% acetone and 30% propanol and other liquids (these percentages are based on the percentage of methane converted) and unreacted methane, were passed from the reactor to a trap. The converted $C_3$ products settled out in the trap and the unreacted methane was recycled back to the reactor. The conversion rate of the methane was about 25% to 30% in a flow system for this particular irradiation period.

The embodiments of the invention in which an exclusive property or privilege is claimed are defined as follows:

1. A process for selectively converting methane to $C_3$ oxygenates comprising:

providing methane in a reaction zone containing a catalyst functional to absorb microwave radiation;

providing a hydrating agent within said reaction zone;

irradiating the methane and hydrating agent reactants in the presence of said catalyst with a pulsed microwave irradiation for a sufficient period of time to selectively convert said reactants to $C_3$ oxygenates; and recovering the $C_3$ oxygenates.

2. The process as set forth in claim 1 wherein said catalyst comprises substantially pure nickel powder, and wherein said hydrating agent comprises water.

3. The process as set forth in claim 1 or 2 wherein said irradiation has a wavelength that is in the range of between about 1.5 to 3.0 GHz and the total irradiation time is about 25 seconds.

4. The process as set forth in claim 1 wherein said catalyst comprises substantially pure nickel powder and said hydrating agent comprises water and a hydrated salt layer positioned beneath said nickel powder.

5. The process as set forth in claim 4 wherein said hydrated salt comprises $CaSO_4.2H_2O$.

6. The process as set forth in claim 5 wherein said irradiation wavelength is in the range of between about 1.5 to 3.0 GHz and the total duration of irradiation is about 25 seconds.

7. The process as set forth in claim 6 wherein the microwave irradiation is provided in pulses of about 0.5 to 10 second with off-times of about 20 to 50 seconds, the cumulative duration of the pulse being about 25 seconds.

* * * * *